(12) United States Patent
Ueno et al.

(10) Patent No.: US 8,569,279 B2
(45) Date of Patent: Oct. 29, 2013

(54) METHOD FOR MODULATING CLAUDIN MEDIATED FUNCTIONS

(75) Inventors: Ryuji Ueno, Montgomery, MD (US); Sachiko Tsukita, Suita (JP)

(73) Assignees: Sucampo AG, Zug (CH); Osaka University, Osaka (JP)

( * ) Notice: Subject to any disclaimer, the term of this patent is extended or adjusted under 35 U.S.C. 154(b) by 60 days.

(21) Appl. No.: 12/853,692

(22) Filed: Aug. 10, 2010

(65) Prior Publication Data
US 2011/0054016 A1    Mar. 3, 2011

Related U.S. Application Data

(63) Continuation-in-part of application No. 12/787,947, filed on May 26, 2010, now abandoned.

(60) Provisional application No. 61/181,463, filed on May 27, 2008.

(51) Int. Cl.
*A01N 43/00* (2006.01)
*A61K 31/33* (2006.01)

(52) U.S. Cl.
USPC .......................................... 514/183; 514/469

(58) Field of Classification Search
USPC ....................................................... 514/469
See application file for complete search history.

(56) References Cited

U.S. PATENT DOCUMENTS

| | | | |
|---|---|---|---|
| 5,073,569 | A | 12/1991 | Ueno et al. |
| 5,166,174 | A | 11/1992 | Ueno et al. |
| 5,212,324 | A | 5/1993 | Ueno |
| 5,221,763 | A | 6/1993 | Ueno et al. |
| 5,739,161 | A | 4/1998 | Ueno |
| 6,242,485 | B1 | 6/2001 | Ueno |
| 6,583,174 | B1 * | 6/2003 | Ueno et al. ............. 514/456 |
| 2005/0192357 | A1 | 9/2005 | Arai et al. |
| 2006/0281818 | A1 | 12/2006 | Ueno et al. |
| 2011/0028541 | A1 | 2/2011 | Tang et al. |

FOREIGN PATENT DOCUMENTS

| | | |
|---|---|---|
| CN | 101318948 A | 12/2008 |
| EP | 0 314 528 A1 | 5/1989 |
| EP | 0 430 552 A2 | 6/1991 |
| EP | 0 758 645 A1 | 2/1997 |
| EP | 0 760 366 A1 | 3/1997 |
| EP | 1 563 846 A1 | 8/2005 |
| JP | 4 300833 A | 10/1992 |
| WO | 03 092617 A2 | 11/2003 |
| WO | 2006 093348 A2 | 9/2006 |
| WO | 2009 104807 A1 | 8/2009 |

OTHER PUBLICATIONS

Demitsu T et al: "Clinical application of new PGE1 drugs to the skin disorders" ACTA Dermatologica, ACTA Dermatologica. Hifuka Kiyo Henshu-Bu, Kyoto, JP, vol. 84, No. 4, Jan. 1, 1989, pp. 553-561.
Mikio Furuse, et al.: Claudin-based tight junctions are crucial for the mammalian epidermal barrier: a lesson from claudin-1-deficient mice; The Journal of Cell Biology, vol. 156, No. 6, Mar. 18, 2002 1099-1111.
Atsushi Tamura, et al.; Megaintestine in Claudin-15-Deficient Mice; Gastroenterology 2008; 134:523-534.
Office Action from State Intellectual Property Office, P.R. China for Application No. 201080023055.4 dated Oct. 26, 2012.

\* cited by examiner

*Primary Examiner* — Brandon Fetterolf
*Assistant Examiner* — Jean Cornet
(74) *Attorney, Agent, or Firm* — Sughrue Mion, PLLC

(57) ABSTRACT

Disclosed is a method for modulating a claudin-mediated function in a mammalian subject which comprises administering to a subject in need thereof an effective amount of a specific fatty acid derivative. The application also discloses a method for treating a dermatological disease and a method for modulating an expression of a claudin in a mammalian subject using the same fatty acid derivative as above.

9 Claims, 2 Drawing Sheets

Compound A −

Compound A +

METHOD FOR MODULATING CLAUDIN MEDIATED FUNCTIONS

CROSS REFERENCES TO THE RELATED APPLICATIONS

This application is a Continuation-In-Part of U.S. application Ser. No. 12/787,947 filed May 26, 2010, which claims priority from U.S. Provisional Application No. 61/181,463 filed May 27, 2009, the disclosures of all of which are hereby incorporated by reference.

TECHNICAL FIELD

The present invention relates to a method and composition for modulating a claudin mediated function. The present invention also relates to a method and composition for treating a dermatological disease. The present invention further relates to a method or composition for modulating an expression of a claudin in a mammalian subject.

BACKGROUND

Epithelial cell sheets have an important role in compartmentalizing various tissues and maintaining their local homeostasis via intercellular barriers consisting of tight junctions (TJs) and in determining the morphogenesis of organs and regulating their functions.

TJs are barrier forming cell-cell junctions that are found in a variety of cell types and tissues, and regulate the barrier activity or permeability of solutes through epithelial cell sheets. Four distinct types of integral membrane proteins have been shown to localize at TJs: occludin, junctional adhesion molecules, claudins, and tricellulin.

Claudins, the major components of tight junction (TJ) strands, which form paracellular barriers, consist of at least 24 family members in mice and humans and now are believed to predominantly constitute functional TJ strands. Evidence has been accumulated that combinations of claudins determine the specific properties of the barrier regarding paracelluar permeability between cells.

Recent functional analyses of claudins in cell cultures and in mice have suggested that claudin-based TJs may have pivotal functions in the regulation of the epithelial microenvironment, which is critical for various biological functions such as control of cell proliferation.

It is reported that continuous Claudin-based TJs occur in the epidermis and Claudin-based tight junctions are crucial for the barrier function of the mammalian skin (J Cell Biol. 2002 Mar. 18; 156(6), 1099-1111, the cited reference is herein incorporated by reference).

Claudin-15 is a type of claudin expressed in many organs of mice in different combinations with other types of claudins. The inventor reported that claudin-15-based formation of TJs to organize the microenvironment including ion conductance is important for normal-sized morphogenesis of the small intestine (Gastroenterology 2008; 134:523-534, the cited reference is herein incorporated by reference).

Prostaglandins (hereinafter, referred to as PG(s)) are fatty acid derivatives, members of class of organic carboxylic acids, which are contained in tissues or organs of human or other mammals, and exhibit a wide range of physiological activity. PGs found in nature (primary PGs) generally have a prostanoic acid skeleton as shown in the formula (A):

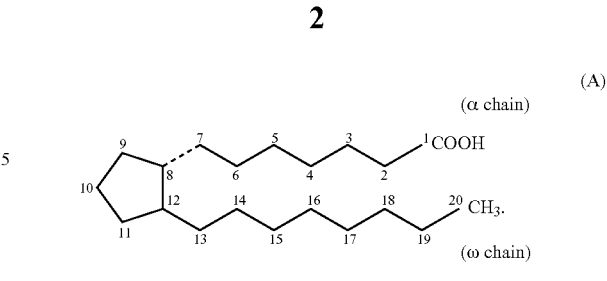

On the other hand, some of synthetic analogues of primary PGs have modified skeletons. The primary PGs are classified into PGAs, PGBs, PGCs, PGDs, PGEs, PGFs, PGGs, PGHs, PGIs and PCJs according to the structure of the five-membered ring moiety, and further classified into the following three types by the number and position of the unsaturated bond at the carbon chain moiety:

Subscript 1: 13,14-unsaturated-15-OH
Subscript 2: 5,6- and 13,14-diunsaturated-15-OH
Subscript 3: 5,6-, 13,14-, and 17,18-triunsaturated-15-OH.

Further, the PGFs are classified, according to the configuration of the hydroxyl group at the 9-position, into α type (the hydroxyl group is of an α-configuration) and β type (the hydroxyl group is of a β-configuration).

PGs are known to have various pharmacological and physiological activities, for example, vasodilatation, inducing of inflammation, platelet aggregation, stimulating uterine muscle, stimulating intestinal muscle, anti-ulcer effect and the like.

Some 15-keto (i.e., having oxo at the 15-position instead of hydroxy)-PGs and 13,14-dihydro (i.e., having single bond between the 13 and 14-position)-15-keto-PGs are fatty acid derivatives known as the substances naturally produced by the action of enzymes during the metabolism of primary PGs.

U.S. Patent application publication No. 2006/0281818 to Ueno et al. (the cited reference is herein incorporated by reference) describes that a specific prostaglandin compound has a significant effect on a conformational change in the TJs that results in recovery of gastrointestinal mucosal barrier function.

DISCLOSURE OF THE INVENTION

The present invention relates to a method for modulating a claudin-mediated function in a mammalian subject, which comprises administering to the subject in need thereof an effective amount of a fatty acid derivative represented by formula (I):

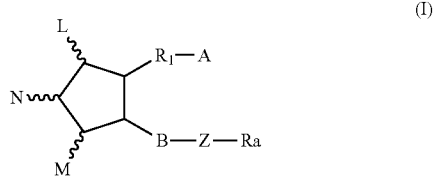

wherein L, M and N are hydrogen, hydroxy, halogen, lower alkyl, hydroxy(lower)alkyl, lower alkanoyloxy or oxo, wherein at least one of L and M is a group other than hydrogen, and the five-membered ring may have at least one double bond;

A is —$CH_3$, or —$CH_2OH$, —$COCH_2OH$, —COOH or a functional derivative thereof;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

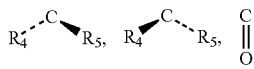

or single bond wherein R$_4$ and R$_5$ are hydrogen, hydroxy, halogen, lower alkyl, lower alkoxy or hydroxy(lower)alkyl, wherein R$_4$ and R$_5$ are not hydroxy and lower alkoxy at the same time;

R$_1$ is a saturated or unsaturated bivalent lower or medium aliphatic hydrocarbon residue, which is unsubstituted or substituted with halogen, lower alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower) alkyloxy; aryl; aryloxy; heterocyclic group; heterocyclic-oxy group.

The present invention also relates to a method for treating dermatological disease in a mammalian subject, which comprises administering to the subject in need thereof an effective amount of the fatty acid derivative represented by formula (I).

The present invention further relates to a method for modulating an expression of a claudin in a mammalian subject, which comprises administering to the subject in need thereof an effective amount of the fatty acid derivative represented by formula (I).

In another aspect, the present invention relates to a pharmaceutical composition for modulating a claudin-mediated function in a mammalian subject which comprises the fatty acid derivative represented by formula (I).

The present invention also relates to a pharmaceutical composition for treating a dermatological disease in a mammalian subject which comprises the fatty acid derivative represented by formula (I).

The present invention further relates to a pharmaceutical composition for modulating an expression of a claudin in a mammalian subject, which comprises the fatty acid derivative represented by formula (I).

In a further aspect, the instant invention provides use of the fatty acid derivative represented by formula (I) for the manufacture of a pharmaceutical composition for modulating claudin-mediated functions in a mammalian subject.

The instant invention also provides use of the fatty acid derivative represented by formula (I) for the manufacture of a pharmaceutical composition for treating a dermatological disease.

The instant invention further provides use of the fatty acid derivative represented by formula (I) for the manufacture of a pharmaceutical composition for modulating an expression of a claudin in a mammalian subject.

DETAILED DESCRIPTION OF THE INVENTION

Figure 1:
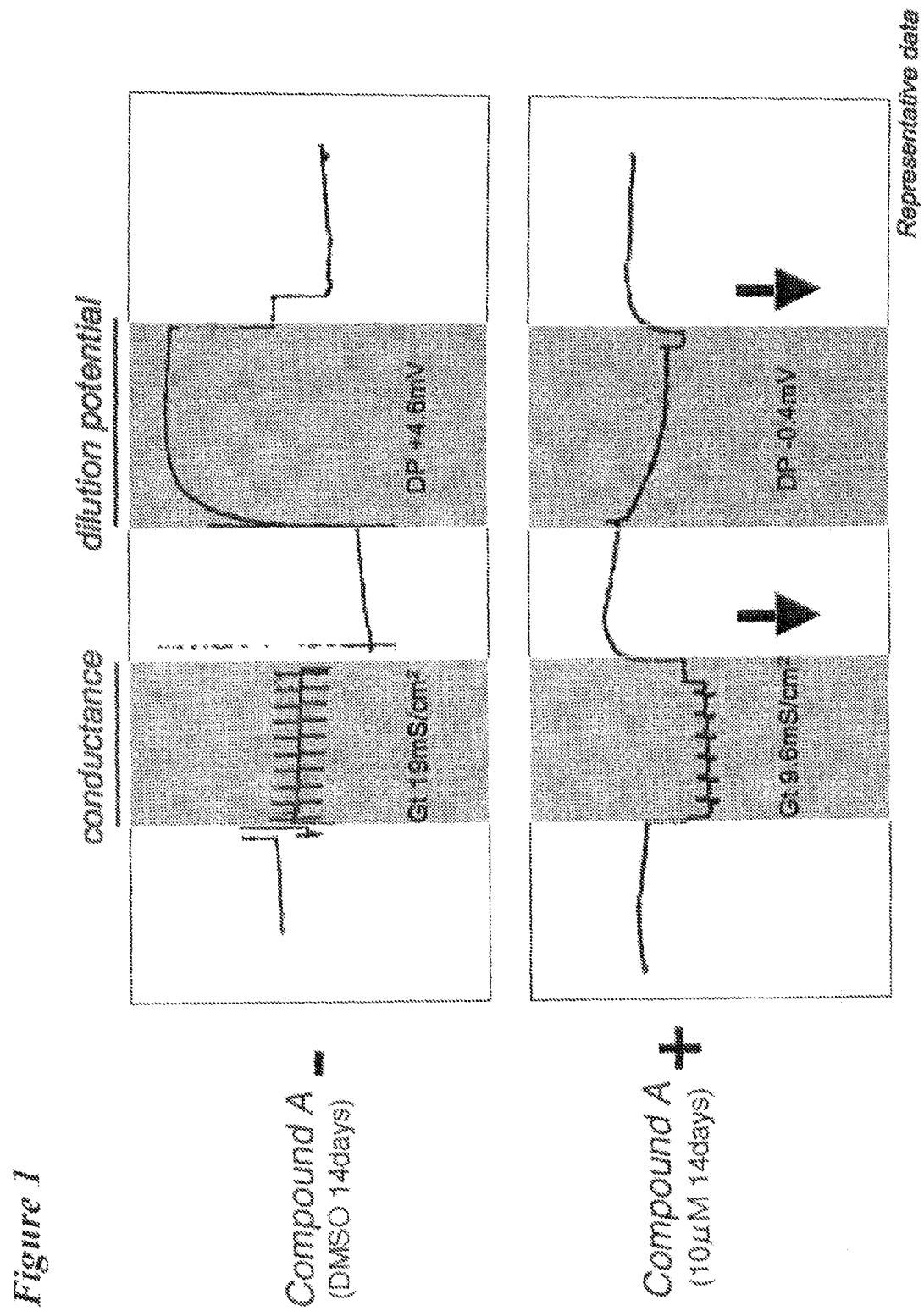
FIG. 1 represents the effect of Compound A [(−)-7-[(2R, 4aR,5R,7aR)-2-(1,1-Difluoropentyl)-2-hydroxy-6-oxooctahydrocyclopenta[b]pyran-5-yl]heptanoic acid] on tight junction permeability and selectivity in male mouse intestine.

The nomenclature of the fatty acid derivative used herein is based on the numbering system of the prostanoic acid represented in the above formula (A).

The formula (A) shows a basic skeleton of the C-20 carbon atoms, but the present invention is not limited to those having the same number of carbon atoms. In the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of the carboxy group (C-1). Similarly, when the number of carbon atoms is decreased in the ω-chain, the number is deleted in the order starting from position 20; and when the number of carbon atoms is increased in the ω-chain, the carbon atoms beyond position 20 are named as substituents. Stereochemistry of the compounds is the same as that of the above formula (A) unless otherwise specified.

In general, each of the terms PGD, PGE and PGF represents a PG compound having hydroxy groups at positions 9 and/or 11, but in the present specification, these terms also include those having substituents other than the hydroxy group at positions 9 and/or 11. Such compounds are referred to as 9-deoxy-9-substituted-PG compounds or 11-deoxy-11-substituted-PG compounds. A PG compound having hydrogen in place of the hydroxy group is simply named as 9- or 11-deoxy-PG compound.

As stated above, the nomenclature of the PG compounds is based on the prostanoic acid skeleton. However, in case the compound has a similar partial structure as a prostaglandin, the abbreviation of "PG" may be used. Thus, a PG compound of which α-chain is extended by two carbon atoms, that is, having 9 carbon atoms in the α-chain is named as 2-decarboxy-2-(2-carboxyethyl)-PG compound. Similarly, a PG compound having 11 carbon atoms in the α-chain is named as 2-decarboxy-2-(4-carboxybutyl)-PG compound. Further, a PG compound of which ω-chain is extended by two carbon atoms, that is, having 10 carbon atoms in the ω-chain is named as 20-ethyl-PG compound. These compounds, however, may also be named according to the IUPAC nomenclatures.

Examples of the analogs (including substituted derivatives) or derivatives include a PG compound of which carboxy group at the end of α-chain is esterified; a compound of which α-chain is extended; physiologically acceptable salt thereof; a compound having a double bond at 2-3 position or a triple bond at position 5-6, a compound having substituent(s) at position 3, 5, 6, 16, 17, 18, 19 and/or 20; and a compound having lower alkyl or a hydroxy (lower) alkyl group at position 9 and/or 11 in place of the hydroxy group.

According to the present invention, preferred substituents at position 3, 17, 18 and/or 19 include alkyl having 1-4 carbon atoms, especially methyl and ethyl. Preferred substituents at position 16 include lower alkyl such as methyl and ethyl, hydroxy, halogen atoms such as chlorine and fluorine, and aryloxy such as trifluoromethylphenoxy. Preferred substituents at position 17 include lower alkyl such as methyl and ethyl, hydroxy, halogen atoms such as chlorine and fluorine, aryloxy such as trifluoromethylphenoxy. Preferred substituents at position 20 include saturated or unsaturated lower alkyl such as C1-4 alkyl, lower alkoxy such as C1-4 alkoxy, and lower alkoxy alkyl such as C1-4 alkoxy-C1-4 alkyl. Preferred substituents at position 5 include halogen atoms such as chlorine and fluorine. Preferred substituents at position 6 include an oxo group forming a carbonyl group. Stereochemistry of PGs having hydroxy, lower alkyl or hydroxy(lower) alkyl substituent at position 9 and/or 11 may be α, β or a mixture thereof.

Further, the above analogs or derivatives may be compounds having an alkoxy, cycloalkyl, cycloalkyloxy, phenoxy or phenyl group at the end of the ω-chain where the chain is shorter than the primary PGs.

A preferred compound used as the fatty acid derivative in the present invention is represented by the formula (II):

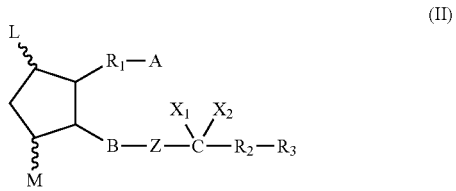

wherein L and M are hydrogen atom, hydroxy, halogen, lower alkyl, hydroxy(lower)alkyl, lower alkanoyloxy or oxo, wherein at least one of L and M is a group other than hydrogen, and the five-membered ring may have one or more double bonds;

A is —$CH_3$, or —$CH_2OH$, —$COCH_2OH$, —COOH or a functional derivative thereof;

B is single bond, —$CH_2$—$CH_2$—, —CH=CH—, —C≡C—, —$CH_2$—$CH_2$—$CH_2$—, —CH=CH—$CH_2$—, —$CH_2$—CH=CH—, —C≡C—$CH_2$— or —$CH_2$—C≡C—;

Z is

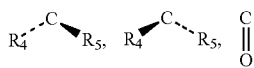

or single bond wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;

$X_1$ and $X_2$ are hydrogen, lower alkyl, or halogen;

$R_1$ is a saturated or unsaturated bivalent lower or medium aliphatic hydrocarbon residue, which is unsubstituted or substituted with halogen, lower alkyl, hydroxy, oxo, aryl or heterocyclic group, and at least one of carbon atom in the aliphatic hydrocarbon is optionally substituted by oxygen, nitrogen or sulfur;

$R_2$ is a single bond or lower alkylene; and $R_3$ is lower alkyl, lower alkoxy, lower alkanoyloxy, cyclo(lower)alkyl, cyclo(lower)alkyloxy, aryl, aryloxy, heterocyclic group or heterocyclic-oxy group.

In the above formula, the term "unsaturated" in the definitions for $R_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 1 to 8 carbon atoms.

The term "halogen atom" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkylene" refers to a straight or branched chain bivalent saturated hydrocarbon group containing 1 to 6 carbon atoms and includes, for example, methylene, ethylene, propylene, isopropylene, butylene, isobutylene, t-butylene, pentylene and hexylene.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tricyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino)ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydroxyl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower) alkyl ester such as hydroxyethyl ester; lower alkoxy(lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydroxyl ester.

The amide of A mean a group represented by the formula —CONR'R", wherein each of R' and R" is hydrogen, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or aryl-sulfonylamides such as methylsulfonylamide, ethylsulfonylamide and tolylsulfonylamide.

Preferred examples of L and M include hydrogen, hydroxy and oxo, and especially, M is hydroxy or hydrogen and L is oxo.

Preferred example of A is —COOH, its pharmaceutically acceptable salt, ester or amide thereof.

Preferred example of $X_1$ and $X_2$ are both being halogen atoms, and more preferably, fluorine atoms, so called 16,16-difluoro type.

Preferred $R_1$ is a hydrocarbon residue containing 1-10 carbon atoms, preferably 6-10 carbon atoms. Further, at least one carbon atom in the aliphatic hydrocarbon is optionally substituted by oxygen, nitrogen or sulfur. Examples of $R_1$ include, for example, the following groups:

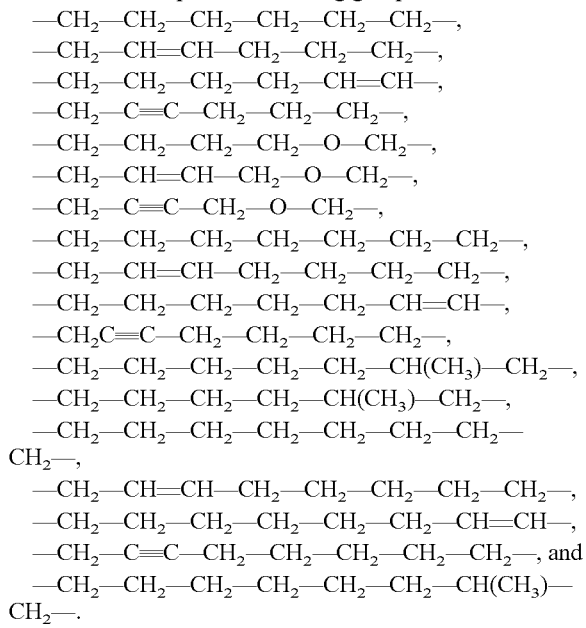

Preferred Ra is a hydrocarbon containing 1-10 carbon atoms, more preferably, 1-8 carbon atoms. Ra may have one or two side chains having one carbon atom.

Preferable compounds include Ra is substituted by halogen and/or Z is C═O in the formula (I), or one of X1 and X2 is substituted by halogen and/or Z is C═O in the formula (II).

Examples of the preferred embodiments are (−)-7-[(2R, 4aR,5R,7aR)-2-(1,1-Difluoropentyl)-2-hydroxy-6-oxooctahydrocyclopenta[b]pyran-5-yl]heptanoic acid, (−)-7-{(2R, 4aR,5R,7aR)-2-[(3S)-1,1-difluoro-3-methylpentyl]-2-hydroxy-6-oxooctahydrocyclopenta[b]pyran-5-yl}heptanoic acid and (−)-7-[(1R,2R)-2-(4,4-difluoro-3-oxooctyl)-5-oxocyclopentyl]heptanoic acid and their functional derivatives.

The configuration of the ring and the α- and/or ω chains in the above formula (I) and (II) may be the same as or different from that of the primary PGs. However, the present invention also includes a mixture of a compound having a primary type configuration and a compound of a non-primary type configuration.

In the present invention, the fatty acid derivative which has saturated bond between 13 and 14, and keto (═O) at 15 position may be in the keto-hemiacetal equilibrium by formation of a hemiacetal between hydroxy at position 11 and keto at position 15.

For example, it has been revealed that when both of $X_1$ and $X_2$ are halogen atoms, especially, fluorine atoms, the compound contains a tautomeric isomer, bicyclic compound.

If such tautomeric isomers as above are present, the proportion of both tautomeric isomers varies with the structure of the rest of the molecule or the kind of the substituent present. Sometimes one isomer may predominantly be present in comparison with the other. However, it is to be appreciated that the present invention includes both isomers.

Further, the 15-keto-PG compounds used in the invention include the bicyclic compound and analogs or derivatives thereof.

The bicyclic compound is represented by the formula (III)

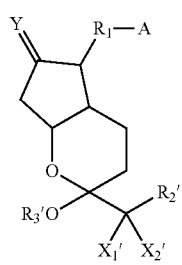

(III)

wherein, A is —CH₃, or —CH₂OH, —COCH₂OH, —COOH or a functional derivative thereof;

$X_1'$ and $X_2'$ are hydrogen, lower alkyl, or halogen;

Y is

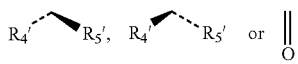

wherein $R_4'$ and $R_5'$ are hydrogen, hydroxy, halogen, lower alkyl, lower alkoxy or hydroxy(lower)alkyl, wherein $R_4'$ and $R_5'$ are not hydroxy and lower alkoxy at the same time.

$R_1$ is a saturated or unsaturated divalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and $R_2'$ is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group.

$R_3'$ is hydrogen, lower alkyl, cyclo(lower)alkyl, aryl or heterocyclic group.

Furthermore, while the compounds used in the invention may be represented by a formula or name based on keto-type regardless of the presence or absence of the isomers, it is to be noted that such structure or name does not intend to exclude the hemiacetal type compound.

In the present invention, any of isomers such as the individual tautomeric isomers, the mixture thereof, or optical isomers, the mixture thereof, a racemic mixture, and other steric isomers may be used in the same purpose.

Some of the compounds used in the present invention may be prepared by the method disclosed in U.S. Pat. Nos. 5,073,569, 5,166,174, 5,221,763, 5,212,324, 5,739,161 and 6,242,485 (these cited references are herein incorporated by reference).

The mammalian subject may be any mammalian subject including a human. The compound may be applied systemically or topically. The compound may be administered by oral administration, intravenous injection (including infusion), subcutaneous injection, intranasal administration, inhalational administration, intra rectal administration, intra vaginal administration, transdermal administration and the like.

The dose may vary depending on the strain of the animal, age, body weight, symptom to be treated, desired therapeutic effect, administration route, term of treatment and the like. A satisfactory effect can be obtained by systemic administration 1-4 times per day or continuous administration at the amount of 0.00001-500 mg/kg per day, more preferably 0.0001-100 mg/kg per day.

The compound may preferably be formulated in a pharmaceutical composition suitable for administration in a conventional manner. The composition may be those suitable for oral administration, intranasal administration, inhalational administration, injection or perfusion as well as it may be an external agent, suppository, pessary or topical dermal dosage forms such as liquid, ointment, paste or patch.

The composition of the present invention may further contain physiologically acceptable additives. Said additives may include the ingredients used with the present compounds such as excipient, diluent, filler, resolvent, lubricant, adjuvant, binder, disintegrator, coating agent, cupsulating agent, ointment base, suppository base, aerosolizing agent, emulsifier, dispersing agent, suspending agent, thickener, tonicity agent, buffering agent, soothing agent, preservative, antioxidant, corrigent, flavor, colorant, functional material such as cyclodextrin and biodegradable polymer, and stabilizer. The additives are well known to the art and may be selected from those described in general reference books of pharmaceutics.

The amount of the above-defined compound in the composition of the invention may vary depending on the formulation of the composition, and may generally be 0.000001-10.0%, more preferably 0.00001-5.0%, most preferably 0.0001-1% by weight base on the total amount of the composition.

Examples of solid compositions for oral administration include tablets, troches, sublingual tablets, capsules, pills, powders, granules and the like. The solid composition may be prepared by mixing one or more active ingredients with at least one inactive diluent. The composition may further contain additives other than the inactive diluents, for example, a lubricant, a disintegrator and a stabilizer. Capsules, tablets and pills may be coated with an enteric or gastroenteric film, if necessary. They may be covered with two or more layers. They may also be adsorbed to a sustained release material, or microcapsulated. Additionally, the compositions may be capsulated by means of an easily degradable material such gelatin. They may be further dissolved in an appropriate solvent such as fatty acid or its mono, di or triglyceride to be a soft capsule. Sublingual tablet may be used in need of fast-acting property.

Examples of liquid compositions for oral administration include emulsions, solutions, suspensions, syrups and elixirs and the like. Said composition may further contain a conventionally used inactive diluents e.g. purified water or ethyl alcohol. The composition may contain additives other than the inactive diluents such as adjuvant e.g. wetting agents and suspending agents, sweeteners, flavors, fragrance and preservatives.

The composition of the present invention may be in the form of spraying composition, which contains one or more active ingredients and may be prepared according to a known method.

Example of the intranasal preparations may be aqueous or oily solutions, suspensions or emulsions comprising one or more active ingredient. For the administration of an active ingredient by inhalation, the composition of the present invention may be in the form of suspension, solution or emulsion which can provide aerosol or in the form of powder suitable for dry powder inhalation. The composition for inhalational administration may further comprise a conventionally used propellant.

Examples of the injectable compositions of the present invention for parenteral administration include sterile aqueous or non-aqueous solutions, suspensions and emulsions. Diluents for the aqueous solution or suspension may include, for example, distilled water for injection, physiological saline and Ringer's solution.

Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. They may be sterilized by filtration through, e.g. a bacteria-retaining filter, compounding with a sterilizer, or by means of gas or radioisotope irradiation sterilization. The injectable composition may also be provided as a sterilized powder composition to be dissolved in a sterilized solvent for injection before use.

The present external agent includes all the external preparations used in the fields of dermatology and otolaryngology, which includes ointment, cream, liquids, lotion, patch and spray.

Another form of the present invention is suppository or pessary, which may be prepared by mixing active ingredients into a conventional base such as cacao butter that softens at body temperature, and nonionic surfactants having suitable softening temperatures may be used to improve absorbability.

According to the present invention, the fatty acid derivatives of the present invention are useful for modulating a claudin-mediated function in a mammalian subject.

The term "claudin-mediated function" as used herein includes cell adhesion, cell proliferation, vasopermeability and epithelial/epidermal barrier function. According to the present invention, one or more of the claudin-mediated functions as above is modulated. The claudin-mediated functions may be the functions of, for example, claudin 1, 4, 7, 8, 10, 11, 12, 15 or 17. Especially the functions of claudin 1, 4 and 15 can be modulated.

The term "modulating" or "modulation" as used herein refers to increasing, decreasing, enhancing, stimulating or inhibiting.

As mentioned above, continuous Claudin-based TJs occurs in the epidermis and Claudin-based tight junctions are crucial for the barrier function of the mammalian skin. Another embodiment of the present invention relates to a method for treating a dermatological disease in a mammalian subject, which comprises administering to the subject in need thereof an effective amount of the fatty acid derivative of formula (I).

The term "dermatological disease" used herein includes any skin disease such as acne, eczema, dermatitis, rosacea, allergic skin disease, skin cancer, skin ulcer (e.g. diabetic skin ulcer) and bedsore (decubitus ulcer). The method of the present invention is preferably for the treatment of skin ulcer, and especially, diabetic skin ulcer. The method of the present invention is also preferably for the treatment of bedsore.

The term "treating" or "treatment" used herein includes any means of control such as prevention, care, relief of the condition, attenuation of the condition and arrest of progression.

The pharmaceutical composition of the present invention may further contain one or more other pharmacological ingredients as far as they do not contradict the purpose of the present invention.

Further details of the present invention will be described as follows with reference to test example, which, however, is not intended to limit the present invention.

Test Example 1

1. Effects of Compound A: (−)-7-[(2R,4aR,5R,7aR)-2-(1,1-Difluoropentyl)-2-hydroxy-6-oxooctahydro-cyclopenta[b]pyran-5-yl]heptanoic Acid on Tissue Conductance and Dilution Potentials in Normal Mouse Intestines (Method) Male C57BL/6 mice (7-8 weeks old) were administered with 10 μM Compound A in the drinking water and fed standard diet for 7 to 14 days. During the period, the mice could drink the water freely. At the conclusion of this period, the mice were sacrificed and the intestines were removed. Approximately 5 cm sections were cut from tip of the jejunum. The intestine section was opened from ventral side, and then it was washed several Limes with Ringer solution. The mucosa of the intestine was carefully stripped from the serosa using forceps. The mucosa was mounted in a standard chamber (5 mm in diameter of exposed surface area) and bathed with buffer solution. Transepithelial short-circuit current (Isc) was measured and total tissue conductance was determined by measuring the current deflections resulting from a 1 mV/min transepithelial pulse and applying Ohm's law. When stable measurement of Isc was achieved, the buffer solution was replaced with potassium-free solution. The solution in the luminal bath were then replaced with the solution containing 75 mM NaCl, 150 mM LiCl, 150 mM KCl, 75 mM $MgCl_2$ and 75 mM $CaCl_2$, in turn, and dilution potentials in each solution were measured.

(Result) As shown in the FIG. 1, Compound A-treated group shows the decrease in conductance and dilution potential of univalent cations compared to no-treatment group.

The result suggests that Compound A induces the change in the properties of the epithelial tight junction.

2. Expression of Claudin Proteins in Mouse Intestine (Method) Treatment of mice and removal of intestine were conducted by similar way mentioned above. The removed intestine was frozen in liquid nitrogen and frozen slices were prepared. Expressions and intracellular distribution of claudin-15 protein were determined with immunofluorescence staining.

Figure 2:
FIG. 2 represents effect of Compound A on the expression of Claudin-15 in mouse intestine.
Figure 2:

(Result) As shown in FIG. 2, expression of claudin-15 protein was decreased in the Compound A-treated group.

(Conclusion) Continuous administration of Compound A caused expression changes of tight junction proteins, such as the decrease of claudin-15 which induces changes of electrophysiological property of the tight junction. Decrease of the expression of claudin-15 in the tight junction resulted to enhance the tightness of the tight junction and strengthen the epithelial sheet against toxic substances.

Test Example 2

Female BKS.Cg−+$Lepr^{db}$/+$Lepr^{db}$/Jcl mice (db/db mice, SPF; CLEA Japan, Inc.), genetically-diabetic mice, were used for the present study. After the removal of the dorsal hair, the skin covering an area of 1.5×1.5 cm centered on the dorsal median was excised using ophthalmic scissors under anesthesia to make a skin ulcer and/or bedsore animal model. Then the excised skin area (ulcer area) was covered with porous film dressing measuring 4×4 cm. The dosing preparation was applied to the ulcer area at a dosage volume of 0.1 mL per site. The application was performed twice a day for 12 days from the day of preparation of the ulcers. Compound B: (−)-7-{(2R,4aR,5R,7aR)-2-[(3S)-1,1-difluoro-3-methylpentyl]-2- hydroxy-6-oxooctahydrocyclopenta[b]pyran-5-yl}heptanoic acid at 10 or 30 micro-g/site was applied to the ulcer per time. The same volume of the vehicle (physiological saline solution containing 1% polysorbate 80: 1% PS80) was applied to the animals in the control group. The day of the start of the application was defined as Day 1. On the Day 1 and Day 13, the frontal edge of the epidermis or the regeneration epidermis of each ulcer was traced on a plastic sheet. The traced ulcer area was measured with an area-line meter. The ulcer area (%) on Day 13 was calculated on the basis of the ulcer area on Day 1. Group mean values with standard errors were calculated for ulcer area (%). The result is shown in Table 1.

TABLE 1

Effect of Compound B on skin ulcer healing in genetically-diabetic mice (db/db mice).

| Test substance | Dosage Micro-g/site | N | Ulcer area, % |
|---|---|---|---|
| Control (1% PS80) | — | 7 | 70.0 ± 5.7 |
| Compound B | 10 | 7 | 43.1 ± 4.2** |
| Compound B | 30 | 7 | 41.1 ± 3.1** |

**$p < 0.01$ compared to control group. (Dunnett's test)

Compound B at 10 and 30 micro-g/site significantly accelerated the ulcer healing as compared to the control group (Table 1). The results suggest that Compound B is useful in the treatment of skin diseases such as skin ulcers, especially diabetic skin ulcers and bedsores.

What is claimed is:

1. A method for treating skin ulcer or bed sore in a mammalian subject, which comprises administering to the subject in need thereof an effective amount of a fatty acid derivative which is (−)-7-{(2R,4aR,5R,7aR)-2-[(3S)-1,1-difluoro-3-methyl]pentyl]-2-hydroxy-6-oxooctahydrocyclopenta[b]pyran-5-yl}heptanoic acid or its salt, or ester.

2. A method for modulating a claudin-mediated function in a mammalian subject, which comprises administering to the subject in need thereof an effective amount of a fatty acid derivative which is (−)-7-{(2R,4aR,5R,7aR)-2-[(3S)-1,1-difluoro-3-methylpentyl]-2-hydroxy-6-oxooctahydrocyclopenta[b]pyran-5-yl}heptanoic acid or its salt, ester.

3. The method as described in claim 2, wherein said claudin is claudin-15.

4. The method as described in claim 2, wherein said claudin-mediated function is epidermal barrier function.

5. A method for modulating an expression of a claudin in a mammalian subject, which comprises administering to the subject in need thereof an effective amount of a fatty acid derivative which is (−)-7-{(2R,4aR,5R,7aR)-2-[(3S)-1,1-difluoro-3-methylpentyl]-2-hydroxy-6-oxooctahydrocyclopenta[b]pyran-5-yl}heptanoic acid or its salt, ester.

6. The method according to claim 5, wherein said claudin is claudin-15.

7. The method as described in claim 1, wherein said fatty acid derivative is (−)-7-{(2R,4aR,5R,7aR)-2-[(3S)-1,1-difluoro-3-methylpentyl]-2-hydroxy-6-oxooctahydrocyclopenta[b]pyran-5-yl}heptanoic acid.

8. The method as described in claim 2, wherein said fatty acid derivative is (−)-7-{(2R,4aR,5R,7aR)-2-[(3S)-1,1-difluoro-3-methylpentyl]-2-hydroxy-6-oxooctahydrocyclopenta[b]pyran-5-yl}heptanoic acid.

9. The method as described in claim 5, wherein said fatty acid derivative is (−)-7-{(2R,4aR,5R,7aR)-2-[(3S)-1,1-difluoro-3-methylpentyl]-2-hydroxy-6-oxooctahydrocyclopenta[b]pyran-5-yl}heptanoic acid.

* * * * *